US006454804B1

(12) United States Patent
Ferree

(10) Patent No.: US 6,454,804 B1
(45) Date of Patent: Sep. 24, 2002

(54) ENGINEERED TISSUE ANNULUS FIBROSIS AUGMENTATION METHODS AND APPARATUS

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 31 days.

(21) Appl. No.: 09/688,716

(22) Filed: Oct. 16, 2000

Related U.S. Application Data

(63) Continuation-in-part of application No. 09/638,726, filed on Aug. 14, 2000, now Pat. No. 6,340,369, which is a continuation-in-part of application No. 09/415,382, filed on Oct. 8, 1999.
(60) Provisional application No. 60/159,488, filed on Oct. 14, 1999.

(51) Int. Cl.[7] .................................................. A61F 2/44
(52) U.S. Cl. ..................... 623/17.11; 424/93.7; 623/908
(58) Field of Search ........................... 623/17.11–17.16, 623/919, 908, 13.11; 427/93.7; 424/93.7

(56) References Cited

U.S. PATENT DOCUMENTS

| | | | |
|---|---|---|---|
| 2,677,369 A | 5/1954 | Knowles ...................... 128/92 |
| 3,366,975 A | 2/1968 | Pangman ......................... 3/36 |
| 3,426,364 A | 2/1969 | Lumb ................................ 3/1 |
| 3,551,560 A | 12/1970 | Thiele .......................... 424/95 |
| 3,593,342 A | 7/1971 | Niebauer ........................... 3/1 |
| 3,648,294 A | 3/1972 | Shahrestani ....................... 3/1 |
| 3,855,638 A | 12/1974 | Pilliar .............................. 3/1 |
| 3,867,728 A | 2/1975 | Stubstad et al. ................... 3/1 |
| 3,875,595 A | 4/1975 | Froning ............................. 3/1 |
| 3,883,902 A | 5/1975 | Lynch ............................. 3/36 |
| 4,229,839 A | 10/1980 | Schwemmer .................. 3/1.91 |
| 4,309,777 A | 1/1982 | Patil ............................. 3/1.91 |
| 4,349,921 A | 9/1982 | Kuntz ............................... 3/1 |
| 4,663,358 A | 5/1987 | Hyon et al. .................... 521/64 |
| 4,707,872 A | 11/1987 | Hessel ........................... 5/451 |
| 4,714,469 A | 12/1987 | Kenna ........................... 623/17 |
| 4,759,766 A | 7/1988 | Buettner-Janz et al. ........ 623/17 |
| 4,772,287 A | 9/1988 | Ray et al. ...................... 623/17 |
| 4,801,299 A * | 1/1989 | Brendel et al. ........... 623/16.11 |
| 4,863,477 A | 9/1989 | Monson ......................... 623/17 |
| 4,874,389 A | 10/1989 | Downey ........................ 623/17 |
| 4,904,260 A | 2/1990 | Ray et al. ...................... 623/17 |
| 4,911,718 A | 3/1990 | Lee et al. ...................... 623/17 |
| 4,917,704 A | 4/1990 | Frey et al. ..................... 623/17 |
| 4,932,969 A | 6/1990 | Frey et al. ..................... 623/17 |
| 4,946,378 A | 8/1990 | Hirayama et al. ............. 623/17 |
| 5,002,576 A | 3/1991 | Fuhrmann et al. ............. 623/17 |
| 5,035,716 A | 7/1991 | Downey ........................ 623/17 |
| 5,047,055 A | 9/1991 | Bao et al. ...................... 623/17 |
| 5,071,437 A | 12/1991 | Steffee ........................... 623/17 |
| 5,108,438 A | 4/1992 | Stone ............................. 623/17 |
| 5,123,926 A | 6/1992 | Pisharodi ....................... 623/17 |
| 5,171,280 A | 12/1992 | Baumgartner .................. 623/17 |
| 5,171,281 A | 12/1992 | Parsons et al. ................. 623/17 |
| 5,192,326 A | 3/1993 | Bao et al. ...................... 623/17 |
| 5,246,458 A | 9/1993 | Graham ......................... 623/17 |
| 5,258,031 A | 11/1993 | Salib et al. .................... 623/17 |
| 5,258,043 A | 11/1993 | Stone ............................. 623/66 |
| 5,314,477 A | 5/1994 | Marnay ......................... 623/17 |
| 5,320,644 A | 6/1994 | Baumgartner ................. 623/17 |
| 5,370,697 A | 12/1994 | Baumgartner ................. 623/17 |
| 5,375,823 A | 12/1994 | Navas ........................... 267/195 |
| 5,401,269 A | 3/1995 | Büttner-Janz et al. ......... 623/17 |
| 5,425,773 A | 6/1995 | Boyd et al. .................... 623/17 |
| 5,458,642 A | 10/1995 | Beer et al. ..................... 623/17 |
| 5,464,439 A * | 11/1995 | Gendler ..................... 623/16.11 |
| 5,514,180 A * | 5/1996 | Heggeness et al. ........ 623/17.11 |
| 5,534,028 A | 7/1996 | Bao et al. ...................... 623/17 |
| 5,534,030 A | 7/1996 | Navarro et al. ............... 623/17 |
| 5,545,229 A * | 8/1996 | Parsons et al. ............ 623/17.11 |
| 5,556,431 A | 9/1996 | Büttner-Janz ................. 623/17 |
| 5,609,635 A | 3/1997 | Michelson .................... 623/17 |
| 5,645,596 A | 7/1997 | Kim et al. ..................... 623/17 |
| 5,645,597 A | 7/1997 | Krapiva ........................ 623/17 |
| 5,674,294 A | 10/1997 | Bainville et al. .............. 623/17 |
| 5,674,296 A | 10/1997 | Bryan et al. .................. 623/17 |
| 5,683,465 A | 11/1997 | Shinn et al. ................... 623/17 |
| 5,702,450 A | 12/1997 | Bisserie ........................ 623/17 |
| 5,711,960 A | 1/1998 | Shikinami .................... 424/426 |
| 5,716,416 A | 2/1998 | Lin ................................ 623/17 |
| 5,800,549 A | 9/1998 | Bao et al. ...................... 623/17 |
| 5,824,093 A | 10/1998 | Ray et al. ...................... 623/17 |
| 5,824,094 A | 10/1998 | Serhan et al. ................. 623/17 |
| 5,865,845 A | 2/1999 | Thalgott ....................... 623/17 |
| 5,865,846 A | 2/1999 | Bryan et al. .................. 623/17 |
| 5,888,226 A | 3/1999 | Rogozinski ................... 623/17 |
| 5,893,889 A | 4/1999 | Harrington .................... 623/17 |
| 5,899,941 A | 5/1999 | Nishijima et al. ............. 623/17 |
| 5,928,284 A | 7/1999 | Mehdizadh .................... 623/17 |
| 6,231,615 B1 * | 5/2001 | Preissman ................. 623/23.73 |
| 6,245,107 B1 * | 6/2001 | Ferree ...................... 623/17.11 |
| 6,332,779 B1 * | 12/2001 | Boyce et al. ................ 433/215 |
| 6,340,369 B1 * | 1/2002 | Ferree ...................... 623/17.11 |

OTHER PUBLICATIONS

North American Spine Society 13 Annual Meeting San Francisco Hilton and Towers Oct. 28–31, 1998; Baron Lonner Md et al. Tissue Engineered Regeneration of the Intervertebral Disc.*

Orthopedics Today, Jul. 2000.

"Proceedings 14th Annual Meeting" North American Spine Society, Oct. 1999.

"Proceedings 13th Annual Meeting" North American Spine Society, Oct. 1998.

* cited by examiner

Primary Examiner—David H. Willse
Assistant Examiner—Suzette J. Jackson
(74) Attorney, Agent, or Firm—Gifford, Krass, Groh, Sprinkle, Anderson & Citkowski, PC

(57) ABSTRACT

Living annulus fibrosis cells are combined with annulus fibrosis extracellular matrix obtained from recently deceased human or animal donors to restore disc function and eliminate pain in patients with disc disease. Additional therapeutic substances like culture medium, growth factors, differentiation factors, hydrogels, polymers, antibiotics, anti-inflammatory medications, or immunosuppressive medications could be added to the transplanted annulus fibrosis tissue. The process can be used to replace or repair other tissues or organs of the body such as the meniscus of the knee.

28 Claims, No Drawings

ENGINEERED TISSUE ANNULUS FIBROSIS AUGMENTATION METHODS AND APPARATUS

REFERENCE TO RELATED APPLICATIONS

This application claims priority of U.S. provisional patent application Serial No. 60/159,488, filed Oct. 14, 1999, and is a continuation-in-part of U.S. patent application Ser. Nos. 09/638,726, filed now U.S. Pat. No. 6,340,369 Aug. 14, 2000; and Ser. No. 09/415,382, filed Oct. 8, 1999, the entire contents of each application being incorporated herein by reference.

FIELD OF THE INVENTION

This invention relates generally to the treatment of diseased or traumatized intervertebral discs, and more particularly, to the use of engineered disc tissues in conjunction with such treatment.

BACKGROUND OF THE INVENTION

Intervertebral discs provide mobility and a cushion between the vertebrae. At the center of the disc is the nucleus pulposus. The nucleus pulposus is surrounded by the annulus fibrosis, which is comprised of cells (fibrocyte-like and chondrocyte-like), collagen fibers, and non-fibrillar extracellular matrix. The components of the annulus are arranged in 15–25 lamellae around the nucleus pulposus. The fibers in the lamellae alternate their direction of orientation by 30 degrees between each band.

The annulus fibrosis has three important functions. First, the annulus contains the nucleus pulposus. Second, the annulus fibrosis, with other ligaments, connects the vertebrae of the spine. Lastly, the annulus fibrosis helps to control movement between the vertebrae.

The fibers of the annulus can tear causing pain and possible extrusion of the nucleus pulposus. Extrusion of the nucleus pulposus is known as a disc herniation. Disc herniations can compress nerves or the spinal cord resulting in arm or leg pain and dysfunction. Surgery to repair disc herniations leaves a hole in the annulus fibrosis. The hole in the annulus acts as a pathway for additional material to protrude into a nerve, resulting in a recurrence of the herniation.

To date, the treatment of tears or defects of the annulus fibrosis has relied for the most part on eliminating the defective disc or disc function. This may be accomplished by fusing the vertebra on either side of the disc. In terms of replacement, prior-art techniques replace either the nucleus or the nucleus and annulus functions. My co-pending U.S. patent application Ser. No. 09/322,516, and Patent Cooperation Treaty Application Serial No. PCT/US/14708 describe methods and devices to occlude annular defects.

SUMMARY OF THE INVENTION

Although transplantation of living cells risks rejection by graft host reaction, this invention broadly recognizes that transplantation of the extracellular matrix of the annulus fibrosis is unlikely to incite graft host reaction. In the preferred embodiment, fibrocytes are harvested, cultured, then added to annulus fibrosis extracellular matrix obtained from recently deceased humans or animals. The combined annulus fibrosis is then introduced into the injured or diseased disc.

The cells or engineered tissues may be introduced using any surgical technique, including percutaneous or laparoscopic approaches. As one delivery mechanism, a passageway may be formed through the annulus fibrosis, with the cells or engineered disc tissue being introduced into the disc through the passageway. In particular, the engineered disc tissue may be sewn or otherwise adhered to the inside or outside of the existing annulus fibrosis using a surgical procedure performed from the posterior or anterior portion of the body.

The method of the invention may further include the step of adding one or more therapeutic substances to the cells or annular tissue prior to transplantation. Such therapeutic substances could include culture media, growth factors, differentiation factors, hydrogels, polymers, antibiotics, anti-inflammatory medications, immunosuppressive medications, or any useful combination thereof.

The teachings of this invention may be combined with any compatible nucleus replacement procedure, as well as the embodiments described in co-pending U.S. patent application Ser. No. 09/690,536 entitled "Annulus Fibrosis Augmentation Methods And Apparatus," the entire contents of which are incorporated herein by reference.

DETAILED DESCRIPTION OF THE INVENTION

Broadly according to the invention, fibrocytes are harvested, cultured, added to annulus fibrosis extracellular matrix material, then sewn or otherwise placed relative to an injured or diseased disc. The annulus fibrosis cells and extracellular matrix are preferably harvested from a live human, though recently deceased human or animal donors may alternatively be used. Depending upon the extent of the harvest, the recipient may function at least in part as a donor, or the tissues from others, including fetal sources, may be used, preferably having a familial relationship to minimize or avoid the need for immunosuppressive substances. Guidelines for tissue procurement including surgical technique of removal, number of hours between death of the donor and tissue procurement, and testing of the donor for infectious disease, are well described.

Following annulus fibrosis harvest, the tissue is processed to kill the living cells. Care is taken to preserve the extracellular matrix. Guidelines for processing the harvested annulus fibrosis as described are well known to those skilled in the art. For example, the tissue could be frozen and thawed.

Fibrocytes are obtained from a tendon of the patient. For example, a palmaris longus tendon could be removed from one arm of the patient. The harvested fibrocytes are isolated and cultured using standard techniques. The harvested sterile tendon is morselized and washed with phosphate buffered saline. The cells are released from the extracellular matrix with 0.2% clostridial collagenase (Worthington CLS II, 140 u/mg) and agitated. See Klagsburn, "Methods in Enzymology, Vol. VII. The resulting suspension is filtered with 153.mu.g.nylon sieve (Tetko, Elmford, N.Y.).

The filtered solution is then centrifuged at 1800 rpm to remove the cells. The supernatant above the cells is removed with a micropipette until the cell concentration reaches $5 \times 10^7$ cells/cc. The harvested cells are grown in Hamm's F-12 culture media, 10% fetal calf serum, L-glutamine (292.mu.g/cc), penicillin (100 u/cc), streptomycin (100.mu.g/cc), and asorbic acid (5.mu.g/cc) at 37° C. The above method is described in U.S. Pat. No. 6,060,053, which is incorporated in its entirety herein by reference.

Precursor cells of the annulus fibrosis, annulus fibrosis cells, chondrocytes, or other living cells that could function like annulus fibrosis cells or that could differentiate into cells to build a functional annulus fibrosis may also be used.

The living cells from cell culture are implanted into the donor extracellular matrix to form a living annulus fibrosis. In the preferred embodiment, the cells are injected into small holes drilled into the donor extracellular matrix.

The living cells and extracellular matrix may be added to the patient's disc immediately after combination or after a period of time to allow attachment of the cells to the matrix. Naturally, in the delayed embodiment, the cells would preferably be supported with culture media.

The engineered annulus is added to the inside or the outside of a patient's annulus. Surgical procedures to access the inner or outer surface of the annulus fibrosis are well known to those skilled in the art. The engineered annulus could be sutured, placed against, or "glued" to the patient's annulus. Platelet rich plasma combined with calcium and thrombin or "fibrin glue" could be used to glue the annular tissues together.

Additional therapeutic substances could be added to the transplanted annulus. For example, resorbable culture medium, tissue growth or differentiation factors (recombinant generated morphogenetic proteins, PDGF, TGF-β, EGF/TGF-α, IGF-I, βFGF), hydrogels, absorbable or nonresorbable synthetic or natural polymers (collagen, fibrin, polyglycolic acid, polylactic acid, polytetrafluoroethylene, etc.), antibiotics, anti-inflammatory medication, immunosuppressive medications, etc. may be used.

In an alternative embodiment, living cells are not added to the harvested annulus fibrosis. The harvested annulus fibrosis is processed as described above to kill the living host annulus cells.

Although annulus fibrosis augmentation and/or transplantation is being described herein in detail, the invention is not limited to treatment of the intervertebral disc. For example, the invention could also be used to treat other tissues of the body such as the meniscus of the knee. In such cases, a meniscus would be removed from recently deceased humans. The harvested meniscus would be processed to kill the cells but preserve the extracellular matrix. Fibroctyes harvested as described above would then be added to the extracellular matrix prior to insertion of the engineered meniscus into a patient's knee. Similarly, chondrocytes could be harvested and added to the meniscus extracellular matrix as described in my pending U.S. Pat. Ser. No. 09/639,309 09/628,727, 09/638,726, and 09/638,242.

Similarly, the process could be used to repair or replace other tissues or organs of the body such as the pancreas, liver, kidney, heart, etc. Healthy live cells would be obtained thorough biopsy and tissue culture. The live cells would be added to the extracellular matrix of tissues or organs harvested to recently deceased human or animals.

I claim:

1. A method of augmenting the annulus fibrosis, comprising the steps of:
    harvesting fibrocytes from a tendon of the patient;
    harvesting the extracellular matrix of the annulus fibrosis from a recently deceased human or animal;
    combining the harvested cells with the extracellular matrix to produce an engineered annulus fibrosis; and
    transplanting the engineered annulus fibrosis into or onto the disc.

2. The method of claim 1, further including the steps of:
    forming a passageway through the disc and transplanting the engineered annulus into the disc through the passageway, or placing the engineered annulus onto the disc.

3. The method of claim 1, further including the step of adding one or more therapeutic substances to the engineered annulus fibrosis.

4. The method of claim 3, wherein the therapeutic substances include one or more of the following:
    culture media, growth factors, differentiation factors, hydrogels, polymers, antibiotics, anti-inflammatory medications, or immunosuppressive medications.

5. The method of claim 1, further including the step of keeping the harvested cells viable until placed into the disc being treated.

6. A method of treating a diseased or traumatized intervertebral disc having a nucleus and annulus fibrosis, comprising the steps of:
    harvesting cells that differentiate into annulus fibrosis cells, or annulus fibrosis cells, or liver cells that function like cells of the annulus fibrosis;
    harvesting the extracellular matrix of the annulus fibrosis from a recently deceased human or animal;
    combining the harvested cells with the extracellular matrix to produce an engineered annulus fibrosis; and
    transplanting the engineered annulus fibrosis into or onto the disc.

7. The method of claim 6, further including the steps of transplanting the engineered annulus fibrosis into or onto the disc.

8. The method of claim 6, further including the step of adding one or more therapeutic substances to the engineered annulus fibrosis.

9. The method of claim 8, wherein the therapeutic substances include one or more of the following:
    culture media, growth factors, differentiation factors, hydrogels, polymers, antibiotics, anti-inflammatory medications, or immunosuppressive medications.

10. The method of claim 6, further including the step of keeping the harvested cells viable until placed into the disc being treated.

11. A method of preparing an engineered annulus fibrosis, comprising the steps of:
    harvesting fibrocytes from a healthy tendon;
    harvesting the extracellular matrix of the annulus fibrosis from a recently deceased human or animal;
    combining the harvested cells with the harvested extracellular matrix to produce an engineered annulus fibrosis; and
    keeping the engineered annulus fibrosis viable until transplantation.

12. An engineered annulus fibrosis according to the method of claim 11.

13. The engineered annulus fibrosis of claim 12.

14. The engineered annulus fibrosis of claim 12, further including one or more therapeutic substances.

15. The engineered annulus fibrosis of claim 12, wherein the therapeutic substances include one or more of the following:
    culture media, growth factors, differentiation factors, hydrogels, polymers, antibiotics, anti-inflammatory medications, or immunosuppressive medications.

16. A method of preparing an engineered annulus fibrosis, comprising the steps of:
    harvesting cells that differentiate into annulus fibrosis like cells, or live cells that function like cells of the annulus fibrosis;
    harvesting the extracellular matrix of the annulus fibrosis from a recently deceased human or animal;

combining the harvested cells with the harvested extracellular matrix to produce an engineered annulus fibrosis; and keeping the engineered annulus fibrosis viable until use.

17. The engineered annulus fibrosis of claim 16, further including one or more therapeutic substances.

18. The engineered annulus fibrosis of claim 17, wherein the therapeutic substances include one or more of the following:

culture media, growth factors, differentiation factors, hydrogels, polymers, antibiotics, anti-inflammatory medications, or immunosuppressive medications.

19. A method of preparing an engineered tissue, comprising the steps of:

harvesting fibrocytes and/or chondrocytes from healthy musculoskeletal tissues;

harvesting the extracellular matrix of musculoskeletal tissues from a recently deceased human or animal; and combining the harvested cells with the harvested extracellular matrix to produce an engineered tissue viable until transplantation.

20. An engineered tissue according to the method of claim 19.

21. The engineered tissue of claim 20, further including one or more therapeutic substances.

22. The engineered tissue of claim 21, wherein the therapeutic substances include one or more of the following:

culture media, growth factors, differentiation factors, hydrogels, polymers, antibiotics, anti-inflammatory medications, or immunosuppressive medications.

23. A method of preparing an engineered tissue, comprising the steps of:

harvesting cells that differentiate into fibrocyte or chondrocyte like cells, or live cells that function like fibrocytes or chondrocytes;

harvesting the extracellular matrix of a musculoskeletal tissue from a recently deceased human or animal; and combining the harvested cells with the harvested extracellular matrix to produce an engineered tissue; and keeping the engineered tissue viable until use.

24. The engineered tissue of claim 23, further including one or more therapeutic substances.

25. The engineered tissue of claim 24, wherein the therapeutic substances include one or more of the following:

culture media, growth factors, differentiation factors, hydrogels, polymers, antibiotics, anti-inflammatory medications, or immunosuppressive medications.

26. A method of preparing an engineered tissue, comprising steps of:

harvesting cells from healthy tissues;

harvesting the extracellular matrix of tissues from a recently deceased human or animal; and combining the harvested cells with the harvested extracellular matrix to produce an engineered tissue viable until transplantation.

27. The engineered tissue of claim 26, further including one or more therapeutic substances.

28. The engineered tissue of claim 27, wherein the therapeutic substances include one or more of the following:

culture media, growth factors, differentiation factors, hydrogels, polymers, antibiotics, anti-inflammatory medications, or immunosuppressive medications.

* * * * *